(12) United States Patent
Chen et al.

(10) Patent No.: US 7,452,696 B2
(45) Date of Patent: Nov. 18, 2008

(54) RECOMBINANT PLASMID AND METHOD FOR EXPRESSING HEPATITIS B VIRAL ANTIGENS AND VIRIONS IN VIVO

(75) Inventors: Pei-Jer Chen, Taipei (TW); Li-Rung Huang, Taipei (TW); Hui-Lin Wu, Taipei (TW); Ding-Shinn Chen, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 11/553,975

(22) Filed: Oct. 27, 2006

(65) Prior Publication Data

US 2008/0124364 A1 May 29, 2008

(51) Int. Cl.
*C12N 15/09* (2006.01)
*C12P 21/04* (2006.01)
*A01N 63/00* (2006.01)
*A61K 39/12* (2006.01)

(52) U.S. Cl. .................. 435/70.1; 424/204.1; 424/93.1; 435/69.3

(58) Field of Classification Search ........................ None
See application file for complete search history.

(56) References Cited

U.S. PATENT DOCUMENTS

2004/0214329 A1* 10/2004 Kay et al. .................. 435/455

2005/0197313 A1* 9/2005 Roelvink et al. ............. 514/44

OTHER PUBLICATIONS

Arad et al., Liver-Targeted Gene Therapy by SV40-Based Vectors Using the Hydrodynamic Injection Method, 2005, Human Gene Therapy, vol. 16, pp. 361-371.*

Priscilla I. Yang, Alana Althage, Josan Chung, Fracis V. Chisari, Hydrodynamic Injection of Viral DNA: A Mouse Model of Acute Hepatitis B Virus Infection, PNAS, Oct. 15, 2002, 13825-13830, vol. 99, No. 21.

F. Liu, Y.K. Song, D. Liu; Hydrodynamics-Based Transfection in Animals by Systemic Administration of Plasmid DNA, Gene Therapy (1999) 6, 1258-1266.

* cited by examiner

*Primary Examiner*—Bruce Campell
*Assistant Examiner*—Benjamin P Blumel
(74) *Attorney, Agent, or Firm*—WPAT, P.C.; Anthony King

(57) ABSTRACT

Disclosed is a recombinant plasmid for expressing hepatitis B viral antigens in vivo, comprising an adeno-associated virus (AVV) vector and a replication-competent hepatitis B virus genome fragment. Mice hydrodynamically injected with the recombinant plasmid of the present invention show persistent expression of hepatitis B viral antigens for more than 6 months in the hepatocytes, thus a immuno-competent mouse model for persistent expression of hepatitis B antigens and also for human chronic hepatitis B virus infection is established, which can be applied in evaluation and elucidation of mechanism of chronic hepatitis and anti-viral drug discovery research.

8 Claims, 5 Drawing Sheets

RECOMBINANT PLASMID AND METHOD FOR EXPRESSING HEPATITIS B VIRAL ANTIGENS AND VIRIONS IN VIVO

BACKGROUND OF THE INVENTION

1. Field of the Invention

The present invention relates to a method for expressing hepatitis B viral antigens and virions in vivo, especially relates to a recombinant plasmid for expressing all of the hepatitis B viral antigens and a method to construct an immunocompetent mouse model for persistently expressing hepatitis B vial antigens by using the recombinant plasmid.

2. The Prior Arts

It is estimated that 350 million people are chronic carriers of hepatitis B virus worldwide, and there are approximately 1 million deaths each year caused by hepatitis B related liver diseases. Evidently, hepatitis B virus has tremendous impact on human health, therefore research for best treatment and new drug discovery enthusiastically become an important healthcare issue.

Hepatitis B virus (HBV) is a partially double-stranded DNA virus that infects human hepatocytes. Upon infection of host individual, the hepatitis B virus will first form a covalently closed circular DNA (cccDNA) within the cell, and then followed by a complicated viral replication process. Host individual infected by hepatitis B virus normally develops acute or chronic necroinflammatory of liver diseases, which consequently may transform into hepatocellular carcinoma. It is generally believed that HBV is not directly cytopathic to the hepatocytes, but HBV mediates the immune response of the infected hepatocytes and triggers the infected cells to express viral antigen, which resulting in host immune system attacking its own infected hepatocytes and eventually leading to cell apotosis.

It is necessary and important to develop an appropriate animal model as a tool in search for new therapy and drug discovery, thus HBV transgenic mice have been proposed to serve as animal models in search for treatment of hepatitis and new drug discovery. The whole-genome HBV transgenic mice are created by delivery of a replication-competent HBV genome into mouse chromosome, in which the inserted viral genome is stably and persistently expressed in the liver tissue. However, it has been found that the mechanism of liver inflammation derived from such HBV transgenic mice is different from scenario of human hepatitis. Furthermore, such HBV transgenic mice are HBV antigen tolerant, thus do not exhibit normal immune response against HBV. Hence, it is concluded that such animal models are not ideal in study of HBV tolerance and clearance.

Chisari et al. devise an approach: by injecting hydrodynamically a recombinant plasmid containing the HBV whole genome into immunologically competent mice, to stimulate HBV replication and to induce hepatitis resembling infection process in human. It is proposed that construction of such readily manipulable animal models may be used for studies of HBV induced immune response and hepatitis. (Chisari et al., (2002) Proc. Natl. Acad. Sci. USA 99 (21), 13825-30). In their study, an inbred mouse B10.D2 that shows strong immune response to the HBV surface antigen is selected as a recipient, and pT-MCS-HBV1.3 plasmid is used as a vector to carry HBV gene. Chisari et al. successfully introduce the recombinant plasmid into mice and elicit immune response that resembles human hepatitis after HBV infection. However, there are disadvantages to this animal model, that is, short-term acute liver inflammatory response and clearance of immune system effect 14 days after transfection. These constraints limit application of such animal model in studies such as long term monitoring of immune response after HBV infection and drug evaluation in chronic hepatitis.

SUMMARY OF THE INVENTION

In order to improve the shortcomings of currently existing acute hepatitis mouse model developed by Chisari et al. for HBV infection studies, it is necessary to develop a mouse model that can persistently express HBV antigens for studies such as hepatitis treatment and drug evaluation. Therefore, the primary object of the present invention is to provide a recombinant plasmid for persistently expressing HBV antigens in an immuno-competent host, which comprises an adeno-associated virus (abbreviated as AAV) vector, and a replication-competent genome fragment of HBV.

Another object of the present invention is to provide a method for expressing HBV antigen in vivo, which comprises the steps of:

(1) providing a recombinant plasmid comprising an AVV vector, and a replication-competent HBV genome fragment; and
(2) delivering the recombinant plasmid to a mouse and transfecting the hepatocytes of the mouse.

When the recombinant plasmid of the present invention is delivered into a mouse and transfected hepatocyes of the injected mouse, it can exist in an episomal form in the hepatocytes of the mouse for more than 200 days, and can be used as a HBV transcription template for production of viral antigens, replication intermediates, and mature virions which are released in bloodstream of the injected mouse. Because the characteristics of episomal form plasmid and the cccDNA of natural infected HBV are very similar, therefore, the recombinant plasmid of the present invention can be used for drug screening and evaluation of effectiveness of cccDNA clearance.

Furthermore, liver histological and serological status analysis of the carrier mouse receiving hydrodynamic injection of the recombinant plasmid of the present invention shows similar pattern to that of healthy HBV carriers in the tolerance stage. The results indicate that with this animal model, it is now possible to address some questions that are hardly studied in the conventional HBV transgenic mouse model, e.g. the tolerance development after HBV exposure, mechanisms of HBV acute exacerbation and the HBV cccDNA clearance in response to antiviral or immuno-modulator therapy etc. Furthermore, the effect of many HBV variants in regulating HBV replication or in contributing to viral persistence may also be conveniently studied in this model.

The present invention is further explained in the following embodiment illustration and examples. Those below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

Figure 1:
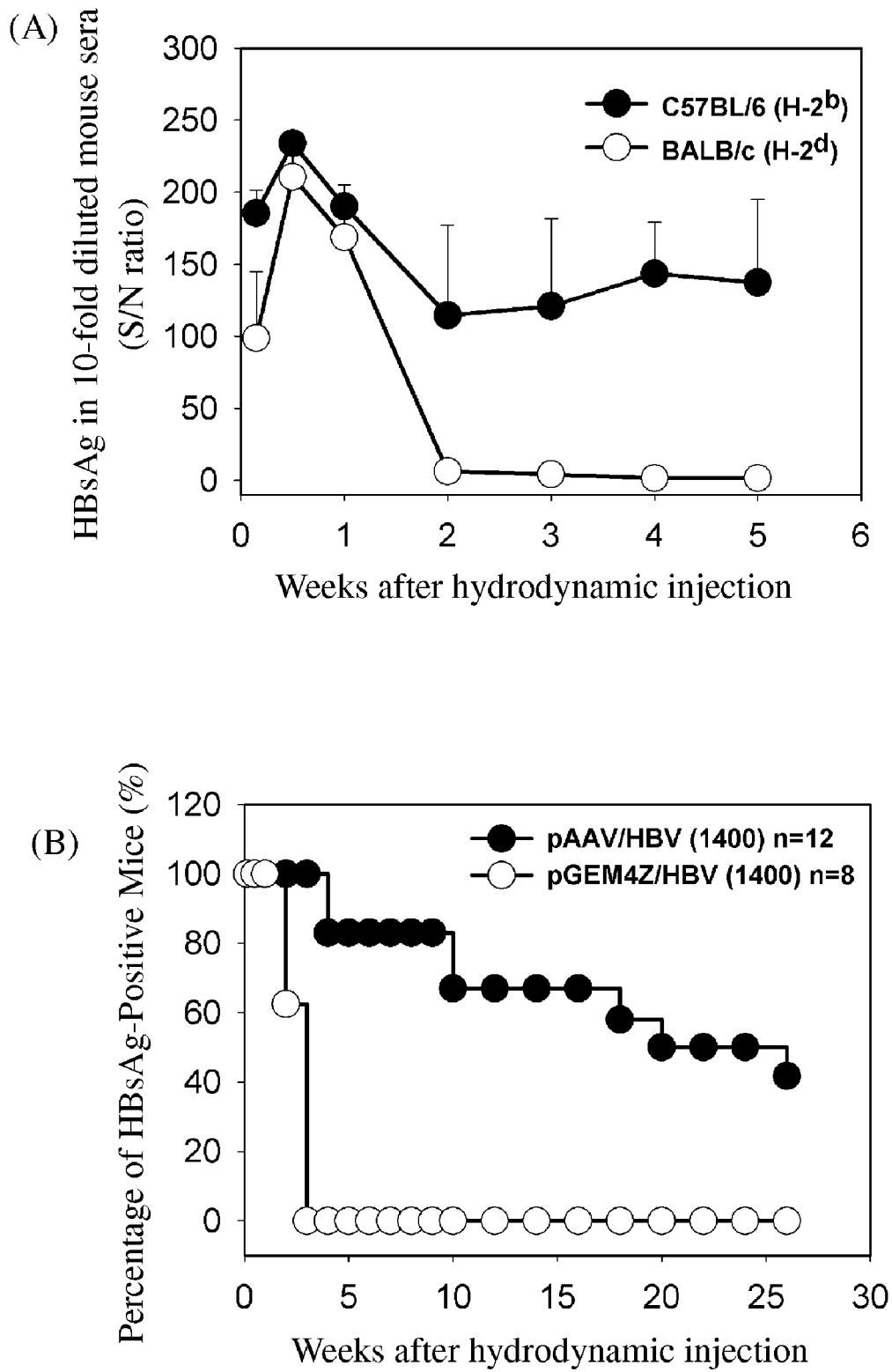
FIG. 1(A) shows temporal profile of HBsAg titer in sera of C57BL/6 and BALB/c mice receiving hydrodynamic injection of the recombinant plasmid pAAV/HBV (1400). S/N ratio greater than 10 is defined as HBsAg-positive; ○:BALB/c mice; ●:C57BL/6 mice.
FIG. 1(B) shows clearance rate of serum HBsAg of C57BL/6 mice receiving hydrodynamic injection of recombinant plasmid pAAV/HBV (1400) and pGEM4Z/HBV (1400). S/N ratio greater than 10 is defined as HBsAg-positive. ○:pGEM4Z/HBV (1400) (n=8); ●:pAAV/HBV (1400) (n=12).

The present invention provides a recombinant plasmid for persistently expressing HBV antigens in vivo, which comprises an adeno-associated virus (AAV) vector and a replication-competent HBV genome fragment.

The abovementioned adeno-associated vector can be any AAV vector that is commercially available, and such commercial vector can be applied in the present invention as vector carrying HBV genome regardless its source. There is no limitation to the HBV genome fragment applied in the present invention, as long as the genome fragment can be inserted into the adeno-associated virus with any conventional method and can subsequently expresses or replicates, such as the genes encoding envelope proteins, core/precore proteins, x protein or polymerase protein of HBV.

In one embodiment, the abovementioned HBV genome fragment is inserted in and flanked by inverted terminal repeats (abbreviated as ITRs) of AAV-GFP plasmid, to replace the Green fluorescent protein (GFP) gene fragment already existed in the plasmid. Thus constructed recombinant plasmid is designated as pAAV/HBV (1400), which DNA sequence is listed as SEQ ID NO: 1. The recombinant plasmid of the present invention is deposited in the Food Industry Research and Development Institute (Taiwan, R.O.C.), with deposit ID No.: BCRC940490.

To persistently express HBV antigens in vivo using the abovementioned expression system, the method can begin with preparation of a recombinant plasmid (for example, pAVV/HBV (1400) plasmid) and follow by delivering the recombinant plasmid into mouse using any known skills in the art, and consequently the hepatocytes of the injected mouse is transfected.

Mice that are well known to those skilled in the art and with immune response level lower than inbred mice B10.D2 (H-2d haplotype) can be used in the present invention, such as C57BL/6 mice (H-2b haplotype), but it should not, however, be considered to limit the scope of the invention. Furthermore, the preferred haplotype of the receiving mouse is H-$2^b$.

In terms of delivery method of the recombinant plasmid, any approach that is well known in the arts of plasmid delivery and transfection of the liver cells can be applied in the present invention, but should not be considered to limit the scope of the present invention. In the present invention, for example, known skills such as hydrodynamic injection can be one of the methods for plasmid delivery. More specifically, in the example of the present invention, transfection of mouse liver cells with the recombinant plasmid is accomplished by hydrodynamic injection of the recombinant plasmid into the tail vein of mice. In order to allow the recombinant plasmid easily injected into tail vein of mice, the plasmid abovementioned is prepared in a biocompatible and non-immunogenic solution, such as phosphate buffer solution, but it should not be considered to limit the scope of the present invention.

Once the recombinant plasmid of the present invention is properly delivered into mice and the hepatocytes are transfected, the plasmids in the hepatocyte are existed as episomal form and are persistently served as templates for transcription for more than 200 days. Moreover the expression of HBV antigens and replication intermediates are also persistently expressed and detected for more than 26 weeks.

Furthermore, because the characteristics of episomal form of the present invention recombinant plasmid are similar to that of the cccDNA in natural HBV infection, liver serological and histological results of the carrier mice of the present invention resemble to that of healthy human carrier. Hence, the recombinant plasmid of the present invention and its application can be applied in construction of mouse models for persistent expression of HBV antigen for more than 6 months.

According to the previous studies of natural HBV infection in human, more than 90% acutely infected adults resolve all clinical symptoms, develop HBeAg- and HBsAg specific antibodies, clear HBeAg and HBsAg from the circulation and maintain lifelong protective immunity. In contrast to HBV infection during adulthood, perinatal HBV infection typically results in chronic hepatitis. In the present invention, different ages of C57BL/6 mice receiving injection of the recombinant plasmid of the present invention also show similar results of age-dependent and carrier rate relationship to that of human exposed to HBV under natural infection condition. Therefore, it is preferred to use young C57BL/6 mice in construction of the mouse model for the persistent expression of HBV antigens in the present invention. However, it is impossible to perform tail vein hydrodynamic injection in immature mice, thus 6- to 8- weeks old mice are preferred choice of the present invention.

By analysis of the HBsAg and HBV DNA produced in the bloodstream during HBV virus particles replication process, we prove that persistent expression of HBV antigens for more than 6 months in the transgenic mice of the presentation is associated with the transfection of the chimeric plasmid of the presentation invention, hence the transgenic animal model of the present invention can be used to elucidate chronic hepatitis mechanism, drug discovery as well as drug evaluation.

Because the present invention is based on the animal model with healthy immunity, thus the induced liver histological and serological status is similar to that of healthy HBV carrier. Consequently the present invention is an ideal model for mechanistic chronic hepatitis studies of hepatitis mechanism and drug evaluation.

EXAMPLE 1

Construction of Vector

The HBV 1.2-full-length DNA is isolated from the plasmid pHBV-48, containing a greater-than-genome-length HBV fragment (subtype adw, gene type A) cloned in pGEM-3Z vector. The replication-competent HBV 1.2-full-length gemone replaced the GFP fragment in AAV-GFP vector by ligation of the BamHI/EcoRI (1.8 kb) and EcoRI/BglII (2.0 kb) fragments of pHBV-48 to the BglII site of AAV-GFP vector. The resulting pAAV/HBV (1400) contains the HBV fragment spanning from nucleotides 1400-3182/1-1987 flanked by inverted terminal repeats (ITRs) of AAV.

EXAMPLE 2

Transfection Procedure and Determination

In vivo experiment of the vector transfection, 6 to 8 weeks old male C57BL/6 mice with H-$2^b$ haplotype are used as experimental group, whereas 6 to 8 weeks old male BALB/c with H-$2^d$ haplotype are selected as control group. Ten micrograms of the abovementioned HBV plasmid pAAV/HBV (1400) were injected into the tail vein of mice in a volume of phosphate-buffered saline (PBS) equivalent to 8% of the mouse body weight under hydrodynamic condition that is well known for those skilled in the art. The total volume is delivered within 5 seconds.

After injection, the mice are regularly bled to follow serum concentration of HBV surface antigen (HBsAg), anti-HBV core protein antibodies (anti-HBc) and anti-HBs antibodies (anti-HBs) at the indicated time points, using the AXSYM system kit (Abbott, GmbH Diagnostica). The livers of mice are preserved in optimal cutting temperature (OCT) for immunohistochemical analysis. Expression of HBcAg and HBsAg in liver of the injected mice is visualized by immunohistochemical staining of liver tissue embedded in OCT by using rabbit anti-HBc or anti-HBs antibodies and Envision_ System HRP (DAB), DAKO Corp., Carpinteria, Calif.).

Changes of serum concentration of HBsAg in experimental group of C57BL/6 mice and the control group BABL/c mice after receiving hydrodynamic injection of the recombinant plasmid of the present invention are shown in FIG. 1. As shown in FIG. 1, when BABL/c (H-$2^d$) received pAAV/HBV (1400) injection, their HBsAg level increased promptly within one week but dropped quickly in two to three weeks. All the mice developed anti-HBs within 14 days.

When the same plasmid of the present invention is injected into experimental group of C57BL/6 mice, their HBsAg level declined much slower. Notably, in about 40% of recipients, the HBsAg could persist for more than 6 months, meeting the definition of persist human HBV infection. In addition, all C57BL/6 transgenic mice receiving hydrodynamic injection of pAAV/HBV plasmid do not develop anti-HBsAb until day 28 after hydrodynamic injection, despite all of them develop anti-HBV core Ab as BALB/c mice.

EXAMPLE 3

The HBV expression cassette is excised by SmaI digestion (located inside of the two ITRs) from the pAAV/HBV (1400) and subcloned into SmaI site of pGEM4Z to result in pGEM4Z/HBV (1400). Then the obtained recombinant plasmid pGEM4Z/HBV (1400) is injected into the tail vein of C57BL/6 mice according to the method described in example 2.

The results show that the injection of pGEM4Z/HBV (1400) into C57BL/6 mice produced only transient surface antigenemia (shown in FIG. 1b) and all of them developed anti-HBs within 4 weeks (Table 1), suggesting that persistence of HBV in C57BL/6 mice is associated with of injection of pAVV/HBV (1400) plasmid.

EXAMPLE 4

HBV viral RNA transcripts and replication intermediates in the liver of C57BL/6 mice receiving injection of recombinant plasmid pAAV/HBV (1400) are detected by analysis of total liver RNA and DNA using well-known Northern Blotting and Southern blotting. In addition, HBsAg and HBcAg in the hepatocytes are examined by immunohistochemical staining. The results are shown in FIG. 2 and FIG. 3.

Figure 2:
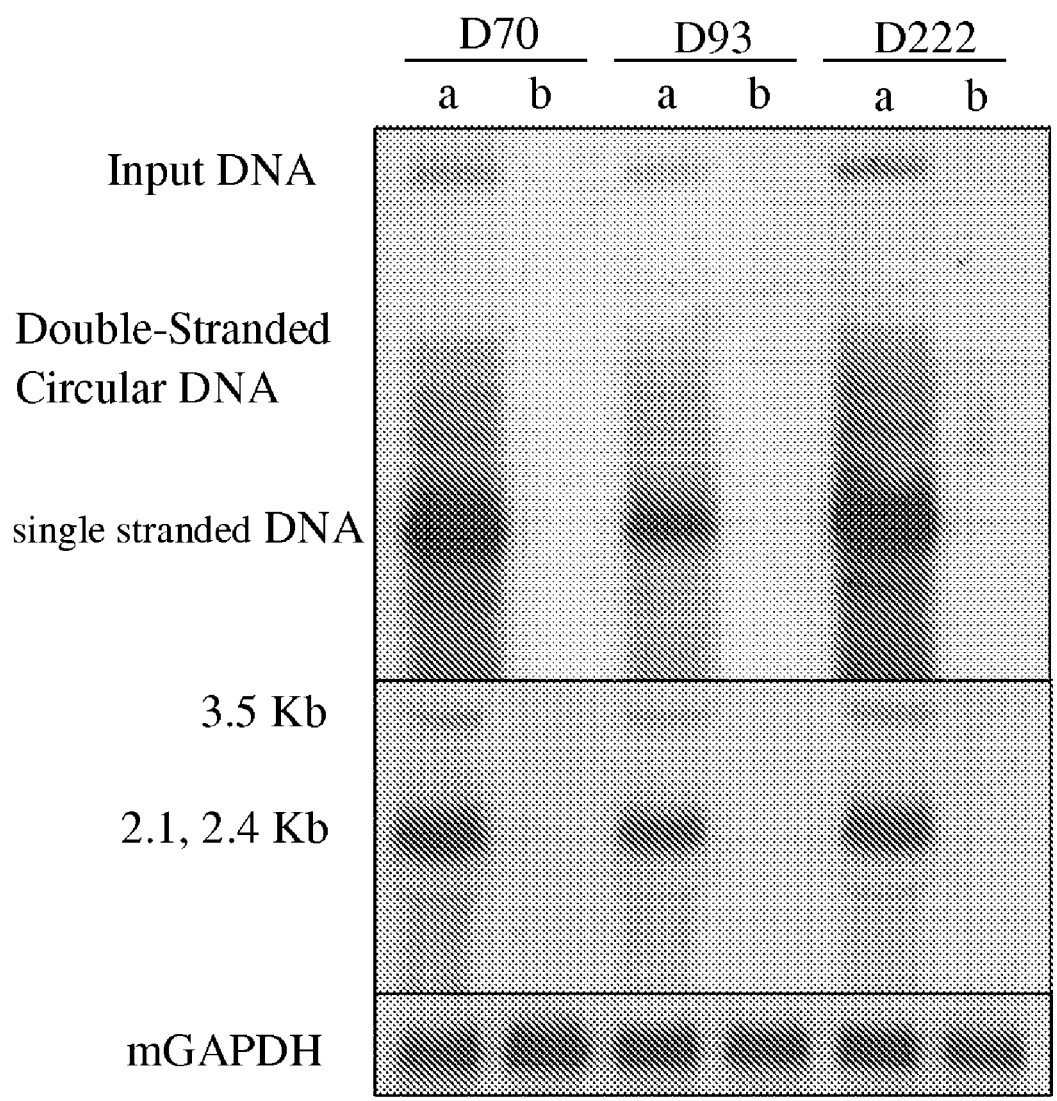
FIG. 2 shows gel electrophoresis analysis of HBV replication intermediates and transcripts in the livers of C57BL/6 mice receiving hydrodynamic injection of plasmid pAAV/HBV (1400). mGAPDH is the internal control of Northern hybridization, lane a is HBsAg-positive C57BL/6 mice, lane b is HBsAg-negative C57BL/6 mice which cleared HBV antigens after hydrodynamic injection of pAAV/HBV (1400).
Figure 3:
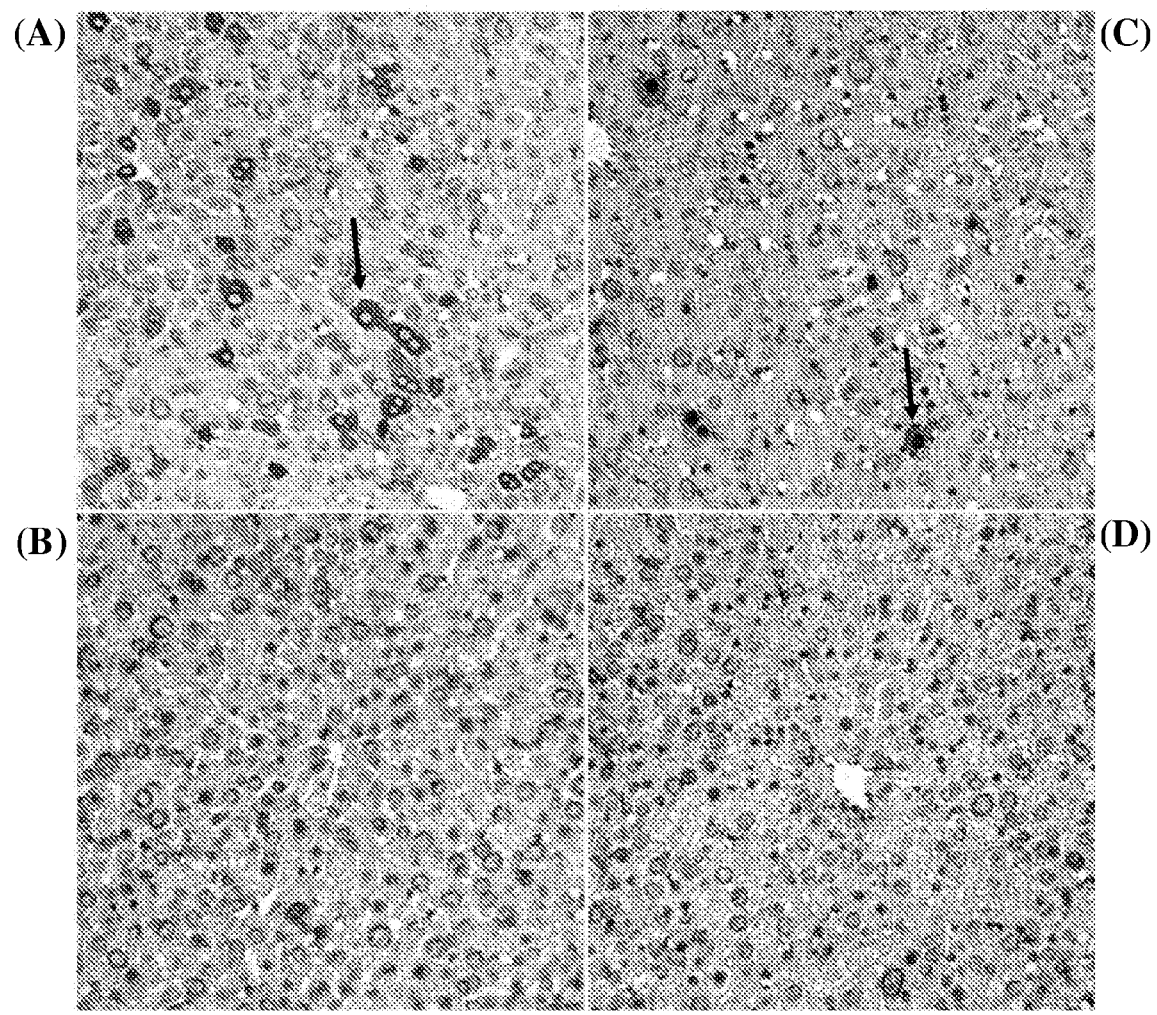
FIG. 3 shows immunohistochemical staining of the liver tissue of the mice receiving hydrodynamic injection of pAVV/HBV (1400) at day 381. Experimental group is HBsAg-positive mice, and control group is HBsAg-negative mice, which cleared HBV antigens after hydrodynamic injection of pAAV/HBV (1400). (A) HBsAg staining of experimental group, arrow indicates HBsAg-positive hepatocytes. (B) HBsAg staining of control group. (C) HBcAg staining of experimental group, arrow indicates HBcAg-positive hepatocytes. (D) HBcAg staining of control group.

As shown in FIG. 2, HBV replication intermediate (including single stranded DNA, double-stranded circular DNA etc.) and RNA transcripts (including 2.1 Kb, 2.4 kb, and 3.5 kb RNA fragment) are detected in the liver of HBsAg-positive C57BL/6 mice at day 70, 93 and 222 after hydrodynamic injection. In addition, HBsAg and HBcAg are also detected in such carrier mice at day 381 after injection (FIG. 3). The results indicate that HBV persistently replicated and survived in the host hepatocytes. Furthermore, long-term expression of HBV in these mice seemed not to cause liver damage as shown by normal ALT level and minimal liver histological change (data not shown).

EXAMPLE 5

According to the method described in example 2, 6.5-week-old male C57BL/6 mice and 13 week-old male C57BL/6 mice, respectively, receive hydrodynamic injection of pAAV/HBV (1400) plasmid in tail vein. Then changes of serum concentration of HBsAg are monitored and analyzed. The results are shown in FIG. 4.

Figure 4:
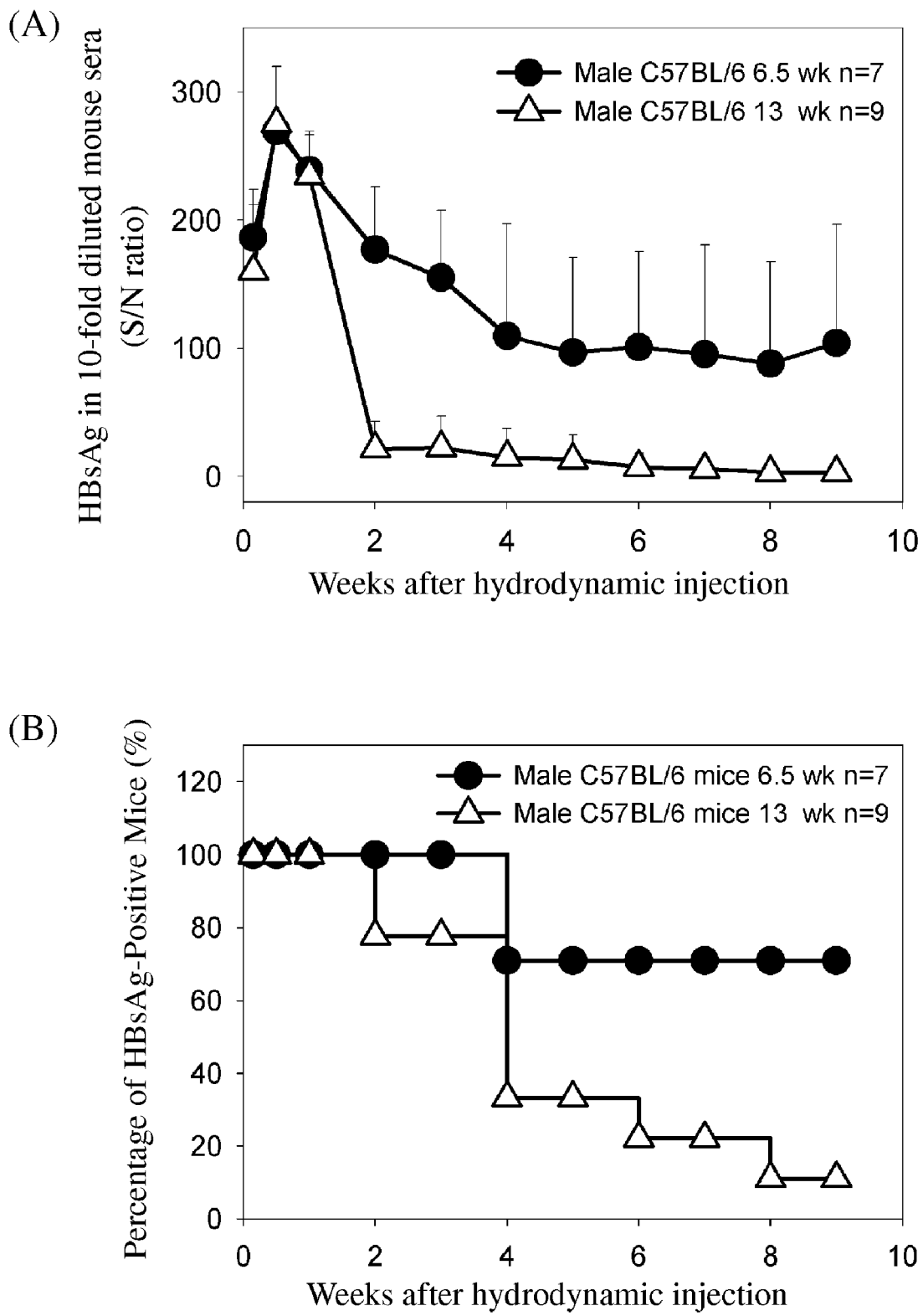
FIG. 4 shows effect of age on HBsAg level of mice receiving hydrodynamic injection of pAAV/HBV (1400). (A) Change of HBsAg titer in bloodstream; Δ:13-week old mice (n=9); ●:6.5-week old mice (n=7). (B) Ratio of HBsAg-positive mice (S/N ratio greater than 10 is defined as HBsAg-positive); Δ:13-week old mice (n=9); ●:6.5-week old mice (n=7).

As shown in FIG. 4, equal amount of HBsAg are detected in the bloodstream of both 6.5- and 13-week-old male C57BL/6 mice in the first week after hydrodynamic injection of pAAV/HBV (1400) plasmid. The HBsAg drops quickly to undetectable level in the group of 13-week-old male mice and more than 90% of them developed neutralizing antibodies (anti-HBs) within 56 days after hydrodynamic injection (FIG. 4b). Only 30% of the 6.5-week-old male mice clear HBsAg in their bloodstream and these mice are also anti-HBs positive (FIG. 4 and Table 2).

EXAMPLE 6

6.5-week-old male and female C57BL/6 mice are hydrodynamically injected with pAAV/HBV (1400) plasmid, respectively, according to the method described in example 2. Then changes of serum concentration of HBsAg are monitored and analyzed. The results are shown in FIG. 5.

Figure 5:
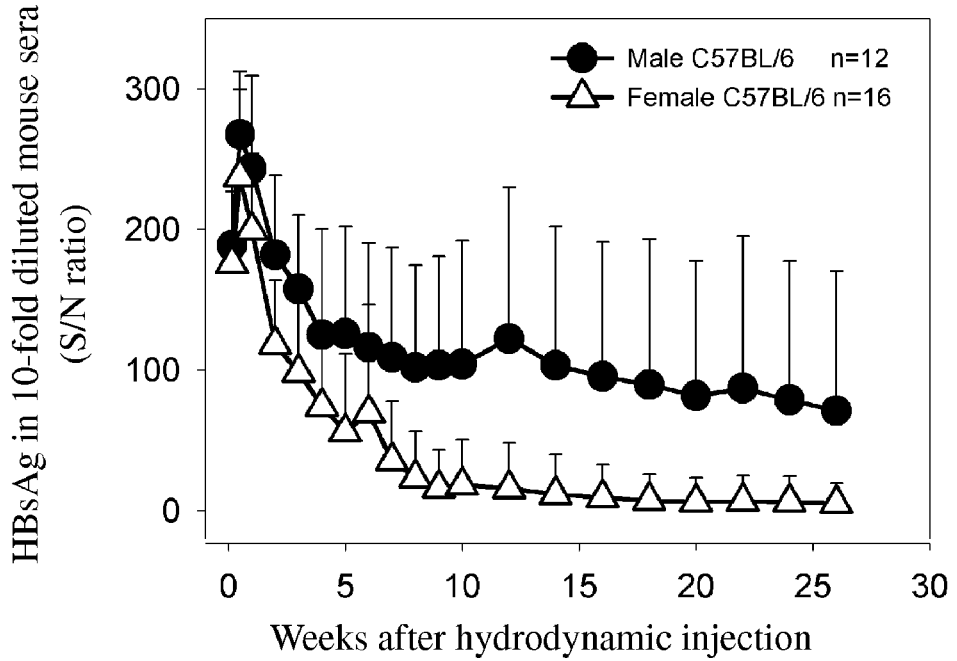
FIG. 5 shows effect of gender on HBsAg level of C57BL/6 mice receiving hydrodynamic injection of pAVV/HBV (1400). (A) Change of HBsAg titer in bloodstream; Δ:female mice (n=16); ●:male mice (n=12). (B) Percentage of HBsAg-positive mice (S/N ratio greater than 10 is defined as HBsAg-positive); Δ:female mice (n=16); ●:male mice (n=12).
Figure 5:
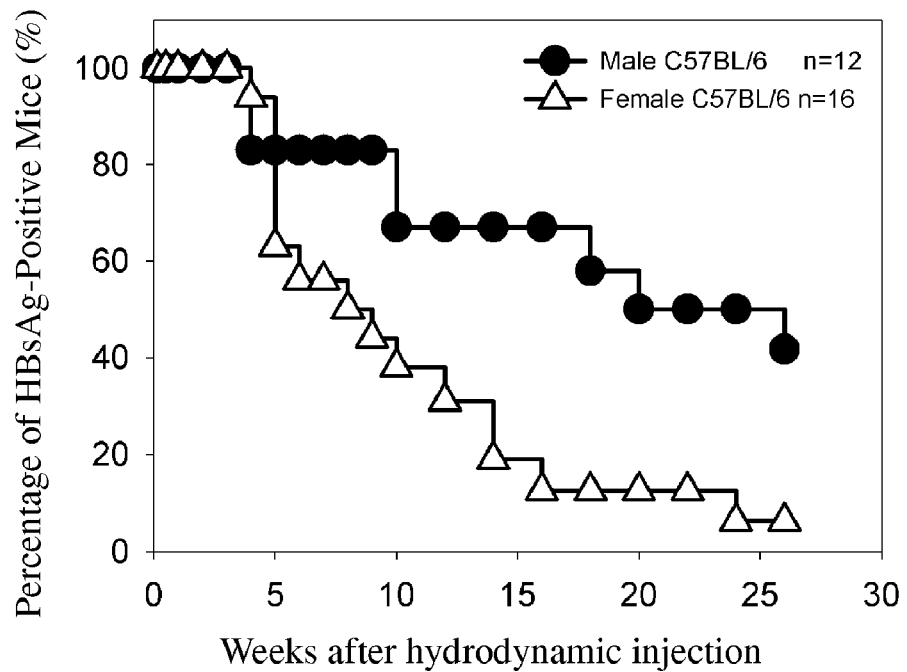

As shown in FIG. 5, after hydrodynamic injection of pAAV/HBV (1400) plasmid, female C57BL/6 mice have lower level of HBsAg than that of male mice. Furthermore, comparing to male mice, female C57BL/6 mice clear HBsAg more rapidly. More than 40% of male C57BL/6 mice are still HBsAg-positive, while less than 10% of the female C57BL/6 mice show HBsAg-positive after hydrodynamic injection.

TABLE 1

The kinetics of antibody production of C57BL/6 and BALB/c mice

| Strain | Plasmid | Anti-HBc Antibody | | Anti-HBs Antibody | | |
|---|---|---|---|---|---|---|
| | | Day 1 | Day 7 | Day 3 | Day 14 | Day 28 |
| C57BL/6 | pAAV/HBV(1400) | 0/9 | 9/9 | 0/9 | 0/9 | 0/9 |
| C57BL/6 | pGEM4Z/HBV(1400) | 0/4 | 4/4 | 0/4 | 0/4 | 4/4 |
| BALB/c | pAAV/HBV(1400) | 0/9 | 9/9 | 0/9 | 9/9 | 9/9 |

TABLE 2

The kinetics of antibody production of C57BL/6 with different age

| Age | Anti-HBc Antibody | | Anti-HBs Antibody Day | | | | |
|---|---|---|---|---|---|---|---|
| | Day 1 | Day 7 | Day 3 | 14 | Day 28 | Day 42 | Day 56 |
| 6.5 wks | 0/14 | 14/14 | 0/14 | 0/14 | 1/14 | 4/14 | 5/14 |
| 13 wks | 0/9 | 9/9 | 0/9 | 0/9 | 3/9 | 8/9 | 9/9 |

What is claimed is:

1. A method for expressing hepatitis B viral antigen in vivo, comprising the steps of:
   (1) providing a recombinant plasmid having the sequence of SEQ ID NO: 1; and
   (2) delivering the recombinant plasmid into a male C57BL/6 mouse and transfecting the hepatocytes of the mouse by hydrodynamic injection;
   wherein an expression of hepatitis B viral antigens persists for more than 26 weeks in the hepatocytes.

2. The method as claimed in claim 1, wherein the mouse is H-$2^b$ haplotype.

3. The method as claimed in claim 1, wherein the age of the mouse is aged 6 to 8 weeks.

4. The method as claimed in claim 1, wherein the recombinant plasmid is prepared in a pre-mix solution before delivering into the mouse.

5. The method as claimed in claim 4, wherein the solution is phosphate buffer.

6. The method as claimed in claim 1, wherein the recombinant plasmid is injected into a tail vein of the mouse.

7. The method as claimed in claim 1, wherein the hepatitis B viral antigen is hepatitis B viral surface antigen.

8. The method as claimed in claim 1, wherein the hepatitis B viral antigen is hepatitis B viral core protein.

* * * * *

SEQUENCE LISTING

<160> NUMBER OF SEQ ID NOS: 1

<210> SEQ ID NO 1
<211> LENGTH: 8058
<212> TYPE: DNA
<213> ORGANISM: hepatitis B virus

<400> SEQUENCE: 1

```
aattcccatc atcaataata taccttattt tggattgaag ccaatatgat aatgagggg      60
tggagtttgt gacgtggcgc ggggcgtggg aacggggcgg gtgacgtagt agtctctaga    120
ggtccccagc gaccttgacg ggcatctgcc cggcatttct gacagctttg tgaactgggt    180
ggccgagaag gaatgggagt tgccgccaga ttctgacatg gatctgaatc tgattgagca    240
ggcaccctg accgtggccg agaagctgca tcgctggcgt aatagcgaag aggcccgcac    300
cgatcgccct tcccaacagt tgcgcagcct gaatggcgaa tggaattcca gacgattgag    360
cgtcaaaatg taggtatttc catgagcgtt tttcctgttg caatggctgg cggtaatatt    420
gttctggata ttaccagcaa ggccgatagt ttgagttctt ctactcaggc aagtgatgtt    480
attactaatc aaagaagtat tgcgacaacg gttaatttgc gtgatggaca gactctttta    540
ctcggtggcc tcactgatta aaaaacact tctcaggatt ctggcgtacc gttcctgtct    600
aaaatccctt taatcggcct cctgtttagc tcccgctctg attctaacga ggaaagcacg    660
ttatacgtgc tcgtcaaagc aaccatagta cgcgccctgt agcggcgcat taagcgcggc    720
gggtgtggtg gttacgcgca gcgtgaccgc tacacttgcc agcgccctag cgcccgctcc    780
tttcgctttc ttcccttcct ttctcgccac gttcgccggc tttccccgtc aagctctaaa    840
tcggggctc cctttagggt tccgatttag tgctttacgg cacctcgacc ccaaaaaact    900
tgattgggt gatggttcac gtagtgggcc atcgccctga tagacggttt ttcgcccttt    960
gacgttggag tccacgttct ttaatagtgg actcttgttc caaactggaa caacactcaa   1020
ccctatctcg gtctattctt ttgatttata agggattttg ccgatttcgg cctattggtt   1080
aaaaaatgag ctgatttaac aaaaatttaa cgcgaatttt aacaaaatat taacgtttac   1140
aatttaaata tttgcttata caatcttcct gttttgggg cttttctgat tatcaaccgg   1200
ggtacatatg attgacatgc tagttttacg attaccgttc atcgcctgca ggggggggg   1260
ggggggggtt ggccactccc tctctgcgcg ctcgctcgct cactgaggcc gggcgaccaa   1320
aggtcgcccg acgcccgggc tttgcccggg cggcctcagt gagcgagcga gcgcgcagag   1380
agggagtggc caactccatc actaggggtt cctagatcct tcgcgggacg tcctttgttt   1440
```

```
acgtcccgtc ggcgctgaat cccgcggacg acccctctcg gggccgcttg ggactctctc    1500
gtccccttct ccgtctgccg ttccagccga ccacggggcg cacctctctt tacgcggtct    1560
ccccgtctgt gccttctcat ctgccggtcc gtgtgcactt cgcttcacct ctgcacgttg    1620
catggagacc accgtgaacg cccatcagat cctgcccaag gtcttacata agaggactct    1680
tggactccca gcaatgtcaa cgaccgacct tgaggcctac ttcaaagact gtgtgtttaa    1740
ggactgggag gagctggggg aggagattag gttaaaggtc tttgtattag gaggctgtag    1800
gcataaattg gtctgcgcac cagcaccatg caacttttc acctctgcct aatcatctct     1860
tgtacatgtc ccactgttca agcctccaag ctgtgccttg ggtggctttg gggcatggac    1920 attacccctta taaagaattt ggagctactg tggagttact ctcgttttg ccttctgact    1980 tttttccttc cgtcagagat ctcctagaca ccgcctcagc tctgtatgag aagccttaga    2040
gtctcctgag cattgctcac ctcaccatac tgcactcagg caagccattc tctgctgggg    2100
ggaattgatg actctagcta cctgggtggg taataatttg gaagatccag catctaggga    2160
tcttgtagta aattatgtta atactaacgt gggtttaaag atcaggcaac tattgtggtt    2220
tcatatatct tgccttactt ttggaagaga gactgtactg gaatatttgg tctctttcgg    2280
agtgtggatt cgcactcctc cagcctatag accaccaaat gccctatct tatcaacact     2340 tccggaaact actgttgtta gacgacggga ccgaggcagg tccctagaa gaagaactcc      2400 ctcgcctcgc agacgcagat ctcaatcgcc gcgtcgcaga agatctcaat ctcgggaatc    2460
tcaatgttag tattccttgg actcataagg tgggaaactt tacggggctt tattcttcta    2520
cagtacctat ctttaatcct gaatggcaaa ctccttcctt tcctaagatt catttacaag    2580
aggacattat aataggtgt caacaatttg tgggccctct cactgtaaat gaaaaaagaa       2640
gattgaaatt aattatgcct gctagattct atcctaccca cactaaatat ttacccttag    2700
acaaaggaat taaaccttat tatccagatc aggtagttaa tcattacttc caaaccagac    2760
attatttaca tactctttgg aaggctggta ttctatataa gagggaaacc acacgtagcg    2820
catcattttg cgggtcacca tattcttggg aacaagagct acagcatggg aggttggtca    2880
tccaaacctc gcaaaggcat ggggacgaat cttttctgttc ccaaccctct gggattcttt    2940
cccgatcatc agttggaccc tgcattcgga gccaactcaa acaatccaga ttgggacttc    3000
aaccccatca agaaccactg gccagcagcc aaccaggtag gagtgggagc attcgggcca    3060
ggactcaccc ctccacacgg cggtattttg gggtggagcc ctcatgctca gggcatattg    3120
accacagtgt caacaattcc tcctcctgcc tccaccaatc ggcagtcagg aaggcagcct    3180
actcccatct ctccacctct aagagacagt catcctcagg ccatgcagtg gaattccact    3240
gccttccacc aagctctgca ggatcccaga gtcagggtc tgtatcttcc tgctggtggc      3300
tccagttcag gaacagtaaa ccctgctccg aatattgcct ctcacatctc gtcaatctcc    3360
gcgaggactg gggaccctgt ggcgaacatg gagaacatca catcaggatt cctaggaccc    3420
ctgctcgtgt tacaggcggg gttttcttg ttgacaagaa tcctcacaat accgcagagt     3480
ctagactcgt ggtggacttc tctcaattt ctaggggat cacccgtgtg tcttggccaa        3540
aattcgcagt ccccaacctc caatcactca ccaacctcct gtcctccaat ttgtcctggt    3600
tatcgttgga tgtgtctgcg gcgttttatc atattcctct tcatcctgct gctatgcctc    3660
atcttcttat tggttcttct ggattatcaa ggtatgttgc ccgtttgtcc tctaattcca    3720
ggatcaacaa caaccagtac gggaccatgc aaaacctgca cgactcctgc tcaaggcaac    3780
```

-continued

```
tctatgtttc cctcatgttg ctgtacaaaa cctacggatg gaaattgcac ctgtattccc    3840
atcccatcgt cctgggcttt cgcaaaatac ctatgggagt gggcctcagt ccgtttctct    3900
tggctcagtt tactagtgcc atttgttcag tggttcgtag gctttcccc cactgtttgg     3960 ctttcagcta tatggatgat gtggtattgg gggccaagtc tgtacagcat cgtgagtccc    4020
tttataccgc tgttaccaat tttcttatgt ctctgggtat acatttaaac cctaacaaaa    4080 caaaagatg gggttattcc ctaaacttca tgggttacat aattggaagt tggagaactt     4140
tgccacagga tcatattgta caaaagatca aacactgttt tagaaaactt cctgttaaca    4200
ggcctattga ttggaaagta tgtcaaagaa ttgtgggtct tttgggcttt gctgctccat    4260
ttacacaatg tggatatcct gccttgatgc ctttgtatgc atgtatacaa gctaaacagg    4320
ctttcacttt ctcgccaact tacaaggcct ttctaagtaa acagtacatg aacctttacc    4380
ccgttgctcg gcaacggcct ggtctgtgcc aagtgtttgc tgacgcaacc cccactggct    4440
ggggcttggc cataggccat cagcgcatgc gtggaacctt tgtggctcct ctgccgatcc    4500
atactgcgga actcctagcc gcttgttttg ctcgcagccg gtctggggca aagctcatcg    4560
gaactgacaa ttctgtcgtc ctctcgcgga aatatacatc atttccatgg ctgctaggct    4620
gtactgccaa ctggatcctt cgcgggacgt cctttgttta cgtcccgtcg gcgctgaatc    4680
ccgcggacga ccctctcgg ggccgcttgg gactctctcg tccccttctc cgtctgccgt     4740
tccagccgac cacggggcgc acctctcttt acgcggtctc ccgtctgtg ccttctcatc     4800 tgccggtccg tgtgcacttc gcttcacctc tgcacgttgc atggagacca ccgtgaacgc    4860
ccatcagatc ctgcccaagg tcttacataa gaggactctt ggactcccag caatgtcaac    4920
gaccgacctt gaggcctact tcaaagactg tgtgtttaag gactgggagg agctggggga    4980
ggagattagg ttaaaggtct ttgtattagg aggctgtagg cataaattgg tctgcgcacc    5040
agcaccatgc aacttttca cctctgccta atcatctctt gtacatgtcc cactgttcaa     5100
gcctccaagc tgtgccttgg gtggctttgg ggcatggaca ttgaccctta taaagaattt    5160
ggagctactg tggagttact ctcgttttg ccttctgact ttttttccttc cgtcagagat    5220 ctaggaaccc ctagtgatgg agttggccac tccctctctg cgcgctcgct cgctcactga    5280
ggccgcccgg gcaaagcccg ggcgtcgggc gaccttggt cgcccggcct cagtgagcga     5340
gcgagcgcgc agagagggag tggccaaccc cccccccc ccctgcag gcgattctct       5400 tgtttgctcc agactctcag gcaatgacct gatagccttt gtagagacct ctcaaaaata    5460
gctaccctct ccggcatgaa tttatcagct agaacggttg aatatcatat tgatggtgat    5520
ttgactgtct ccggcctttc tcacccgttt gaatctttac ctacacatta ctcaggcatt    5580
gcatttaaaa tatatgaggg ttctaaaaat ttttatcctt gcgttgaaat aaaggcttct    5640
cccgcaaaag tattcaggg tcataatgtt tttggtacaa ccgatttagc tttatgctct     5700
gaggctttat tgcttaattt tgctaattct ttgccttgcc tgtatgattt attggatgtt    5760
ggaattcctg atgcggtatt ttctccttac gcatctgtgc ggtatttcac accgcatatg    5820
gtgcactctc agtacaatct gctctgatgc cgcatagtta agccagcccc gacacccgcc    5880
aacacccgct gacgcgccct gacgggcttg tctgctcccg gcatccgctt acagacaagc    5940
tgtgaccgtc tccgggagct gcatgtgtca gaggttttca ccgtcatcac cgaaacgcgc    6000
gagacgaaag ggcctcgtga tacgcctatt tttataggtt aatgtcatga ataataatggt   6060
```

-continued

```
ttcttagacg tcaggtggca cttttcgggg aaatgtgcgc ggaacccta tttgtttatt      6120
tttctaaata cattcaaata tgtatccgct catgagacaa taaccctgat aaatgcttca      6180
ataatattga aaaaggaaga gtatgagtat tcaacatttc cgtgtcgccc ttattcsctt      6240
ttttgcggca ttttgccttc ctgttttttgc tcacccagaa acgctggtga aagtaaaaga     6300
tgctgaagat cagttgggtg cacgagtggg ttacatcgaa ctggatctca acagcggtaa      6360
gatccttgag agttttcgcc ccgaagaacg ttttccaatg atgagcactt ttaaagttct      6420
gctatgtggc gcggtattat cccgtattga cgccgggcaa gagcaactcg gtcgccgcat      6480
acactattct cagaatgact tggttgagta ctcaccagtc acagaaaagc atcttacgga      6540
tggcatgaca gtaagagaat tatgcagtgc tgccataacc atgagtgata acactgcggc      6600
caacttactt ctgacaacga tcggaggacc gaaggagcta accgcttttt tgcacaacat      6660
ggggatcat gtaactcgcc ttgatcgttg ggaaccggag ctgaatgaag ccataccaaa       6720
cgacgagcgt gacaccacga tgcctgtagc aatggcaaca acgttgcgca aactattaac      6780
tggcgaacta cttactctag cttcccggca acaattaata gactggatgg aggcggataa     6840
agttgcagga ccacttctgc gctcggccct tccggctggc tggtttattg ctgataaatc      6900
tggagccggt gagcgtgggt ctcgcggtat cattgcagca ctggggccag atggtaagcc      6960
ctcccgtatc gtagttatct acacgacggg gagtcaggca actatggatg aacgaaatag      7020
acagatcgct gagataggtg cctcactgat taagcattgg taactgtcag accaagttta      7080
ctcatatata ctttagattg atttaaaact tcatttttaa tttaaaagga tctaggtgaa      7140
gatccttttt gataatctca tgaccaaaat cccttaacgt gagttttcgt tccactgagc      7200
gtcagacccc gtagaaaaga tcaaaggatc ttcttgagat cctttttttc tgcgcgtaat      7260
ctgctgcttg caaacaaaaa aaccaccgct accagcggtg gtttgtttgc cggatcaaga      7320
gctaccaact cttttttccga aggtaactgg cttcagcaga gcgcagatac caaatactgt      7380
ccttctagtg tagccgtagt taggccacca cttcaagaac tctgtagcac cgcctacata      7440
cctcgctctg ctaatcctgt taccagtggc tgctgccagt ggcgataagt cgtgtcttac      7500
cgggttggac tcaagacgat agttaccgga taaggcgcag cggtcgggct gaacggggg      7560
ttcgtgcaca cagcccagct tggagcgaac gacctacacc gaactgagat acctacagcg      7620
tgagctatga gaaagcgcca cgcttcccga agggagaaag gcggacaggt atccggtaag      7680
cggcagggtc ggaacaggag agcgcacgag ggagcttcca gggggaaacg cctggtatct      7740
ttatagtcct gtcgggtttc gccacctctg acttgagcgt cgatttttgt gatgctcgtc      7800
agggggcgg agcctatgga aaaacgccag caacgcggcc ttttacggt tcctggcctt       7860
ttgctggcct tttgctcaca tgttctttcc tgcgttatcc cctgattctg tggataaccg      7920
tattaccgcc tttgagtgag ctgataccgc tcgccgcagc cgaacgaccg agcgcagcga      7980
gtcagtgagc gaggaagcgg aagagcgccc aatacgcaaa ccgcctctcc ccgcgcgttg      8040
gccgattcat taatgcag                                                    8058
```